US006482531B1

(12) United States Patent
Timmons et al.

(10) Patent No.: US 6,482,531 B1
(45) Date of Patent: Nov. 19, 2002

(54) NON-FOULING, WETTABLE COATED DEVICES

(75) Inventors: Richard B. Timmons, Arlington, TX (US); Jenn-Hann Wang, Mission Viejo, CA (US); Charles R. Savage, Arlington, TX (US); Yuliang Wu, Arlington, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 09/115,860

(22) Filed: Jul. 15, 1998

Related U.S. Application Data

(63) Continuation-in-part of application No. 08/632,935, filed on Apr. 16, 1996, now Pat. No. 5,876,753.
(60) Provisional application No. 60/055,260, filed on Aug. 8, 1997.

(51) Int. Cl.$^7$ .................. B32B 27/30; B32B 31/00; G02C 7/04
(52) U.S. Cl. .................. 428/500; 428/936; 523/106; 525/937; 427/446; 427/447; 427/450
(58) Field of Search .................. 428/411.1, 480, 428/482, 483, 500, 515, 936; 523/106; 525/937; 427/446, 447, 450; 351/160 R

(56) References Cited

U.S. PATENT DOCUMENTS

| | | | |
|---|---|---|---|
| 3,008,920 A | 11/1961 | Urchick | 260/45.5 |
| 3,070,573 A | 12/1962 | Beck | 260/45.5 |
| 3,854,982 A | 12/1974 | Aelion et al. | 117/68 |
| 3,916,033 A | 10/1975 | Merrill | 427/36 |
| 3,925,178 A | 12/1975 | Gesser et al. | 204/165 |
| 3,939,049 A | 2/1976 | Ratner et al. | 204/159.13 |
| 4,143,949 A | 3/1979 | Chen et al. | 351/160 |
| 4,311,573 A | 1/1982 | Mayhan et al. | |
| 4,585,666 A | 4/1986 | Lambert | 427/2 |
| 4,589,964 A | 5/1986 | Mayhan et al. | 522/85 |
| 4,693,799 A | 9/1987 | Yanagihara et al. | 204/165 |
| 4,880,687 A | 11/1989 | Yokoyama et al. | 428/141 |
| 4,919,659 A | 4/1990 | Horbett et al. | 623/1 |
| 5,002,794 A | * 3/1991 | Ratner et al. | 427/41 |
| 5,002,974 A | 3/1991 | Geria | 514/782 |
| 5,007,928 A | 4/1991 | Okamura et al. | 623/6 |
| 5,034,265 A | 7/1991 | Hoffman et al. | |
| 5,091,204 A | 2/1992 | Ratner et al. | |
| 5,153,072 A | * 10/1992 | Ratner et al. | 428/461 |
| 5,171,267 A | 12/1992 | Ratner et al. | |
| 5,196,458 A | 3/1993 | Nunez et al. | 523/106 |
| 5,304,584 A | 4/1994 | Nunez et al. | 523/106 |
| 5,451,428 A | 9/1995 | Rupp | 427/2.12 |
| 5,630,946 A | 5/1997 | Hart et al. | 210/805 |
| 5,871,823 A | * 2/1999 | Anders et al. | 427/512 |

FOREIGN PATENT DOCUMENTS

| | | | |
|---|---|---|---|
| DE | 195 48 152 | 6/1997 | |
| EP | 0 574 352 A1 | 2/1993 | 291/18 |
| JP | 63 075002 | 4/1988 | |
| WO | WO 87 01040 | 2/1987 | |
| WO | PCT/US90/05032 | 9/1990 | |
| WO | WO 95 04609 | 2/1995 | |
| WO | WO 97 22631 | 6/1997 | |
| WO | WO 97 38801 | 10/1997 | |

OTHER PUBLICATIONS

Odian, George, "Principles of Polymerization", 3rd Edition, p. 267, Dec. 1991.*

K. Nakajima, A.T. Bell and M. Shen, "Plasma Polymerization of Tetrafluoroethylene," Journal of Applied Polymer Science, vol. 23, pp. 2627–2637, Jan. 1979.

H. Yasuda and T. Hsu, "Some Aspects of Plasma Polymerization Investigated by Pulsed R.F. Discharge," Journal of Polymer Science, vol. 15, pp. 81–97, Jan. 1977.

Gabriel P. Lopez, Buddy D. Ratner, Caren D. Tidwell, Claire L. Haycox, Richard J. Rapoza and Thomas A. Horbett, "Glow Discharge Plasma Deposition of Tetraethylene Glycol Dimethyl Ether for Fouling–Resistant Biomaterial Surfaces," Journal of Biomedical Materials Research, vol. 26, pp. 415–439, Jan. 1992.

V. Panchalingam, Bryan Poon, Hsiao–hwei Huo, Charles R. Savage, Richard B. Timmons and Robert C. Eberhart, "Molecular Surface Tailoring of Biomaterials via Pulsed EF Plasma Discharges," J. Biomater Sci. Polymer Edn., vol. 5, No. 1/2, pp. 131–145, Jan. 1993.

V. Panchalingam, X. Chen, Charles R. Savage, Richard B. Timmons and Robert C. Eberhart, "Molecular Tailoring of Surfaces via Pulsed RF Plasma Depositions," Journal of Applied Polymer Science: Applied Polymer Symposium 54, pp. 123–141, Jan. 1994.

Dierk Beyer, Wolfgang Knoll, Helmut Ringsdorf, Jenn–Hann Wang, Richard B. Timmons, and Peter Sluka, "Reduced Protein Adsorption on Plastics via Direct Plasma Deposition of Triethylene Glycol Monoallyl Ether," John Wiley & Sons, Inc., pp. 181–189, Jan. 1997.

E.E. Johnston, B.D. Ratner and J.D. Bryers, "RF Plasma Deposited PEO–Like Surfaces that Inhibit *Pseudomonas aruginosa* Accumulation," Polymeric Materials Science and Engineering, vol. 77, Jan. 1997, p. 577.

* cited by examiner

*Primary Examiner*—Paul Thibodeau
*Assistant Examiner*—Ramsey Zacharia
(74) *Attorney, Agent, or Firm*—Jackson Walker L.L.P.

(57) ABSTRACT

A device, and its production method, the device has a substrate and a coating composition, the coating composition being formed by the gas phase or plasma polymerization of a gas comprising at least one organic compound or monomer. The polymerization is carried out using a pulsed discharge having a duty cycle of less than about ⅕, in which the pulse-on time is less than about 100 msec and the pulse-off time is less than about 2000 msec. The duty cycle can also be varied, thus the coating composition can be gradient layered accordingly. The device has a coating composition which is uniform in thickness, pin-hole free, optically transparent in the visible region of the magnetic spectrum, permeable to oxygen, abrasive resistant, wettable and biologically non-fouling.

14 Claims, 5 Drawing Sheets

NON-FOULING, WETTABLE COATED DEVICES

This application claims the benefit of U.S. Provisional Application Serial No. 60/055,260 filed on Aug. 8, 1997, and entitled "NON-FOULING WETTABLE COATED DEVICES," commonly assigned with the present invention and incorporated herein by reference.

This is a continuation-in-part application of prior U.S. patent application Ser. No. 08/632,935 now U.S. Pat. No. 5,876,753, filed Apr. 16, 1996, the entire content of which is hereby incorporated by reference.

The U.S. Government has certain rights in the present invention pursuant to the National Institutes of Health under Grant R01 AR43186-01 and by the State of Texas through the Texas Higher Education Coordinating Board ATP Program under Grant 003656-137.

TECHNICAL FIELD

This invention relates to devices having gas-phase deposited coatings and their methods of production. More specifically, this invention relates to devices, and their method of production, having gas-phase deposited coatings which are non-fouling and wettable.

BACKGROUND

The chemical composition of surfaces plays a pivotal role in dictating the overall efficacy of many devices. Some devices require non-fouling, and wettable surfaces in order for the devices to be useful for their intended purposes. For example, many biomedical devices such as catheters, stents, implants, interocular lenses and contact lenses require surfaces which are biologically non-fouling, which means that proteins, lipids, and cells will not adhere to the surfaces of the devices. In some cases materials for devices are developed which have all the necessary attributes for their intended purposes, such as, strength, optimal transmission, flexibility, stability, and gas transport except that the surfaces of the materials will foul when in use. In these cases either new materials for the devices are developed or an attempt to change the surface characteristics of the materials is made.

In the specific case of contact or interocular lenses, particularly contact lenses, although many polymeric materials possess the necessary mechanical, oxygen permeation and optical properties required for lens manufacture, many potential contact lens materials are subject to rapid biological fouling due to the adhesion of proteins, lipids, and other molecules present in the tear fluid surrounding the lens, and/or the surface energies of the materials are too low making the contact lenses too hydrophobic, and therefore not wettable by the tear fluid.

In light of the above considerations, a common approach utilized by various researchers is to attempt to improve the biocompatibility of the potential contact lens materials by application of a thin coating to these substrates. In theory such a coating would take advantage of the inherent favorable bulk mechanical, gas transport and optical properties of the polymer with the applied coating providing the required hydrophilicity and non-fouling properties. However, despite the plethora of such studies, it is significant to note that, at present, not a single contact lens manufacturer offers commercial products having coatings applied for this express purpose. Obviously, although the concept of simply applying a surface coating to remedy physical property deficiencies of a given polymer substrate has theoretical appeal, this has proven to be a totally illusive goal in actual practice. The previous failures reflect the fact that, to be commercially viable, a successful contact lens coating procedure must satisfy a myriad of rather stringent requirements. These requirements, as a minimum, include the following criteria: the coatings must be uniform and, ideally, pin-hole free; the coatings must be both wettable and non-biologically fouling; the coatings should be essentially devoid of extractables and they must exhibit long-term chemical stability in aqueous saline solution; the coatings must exhibit excellent optical transparency in the visible region of the electromagnetic spectrum; the coatings must not compromise the oxygen permeability (i.e., the so-called DK value) of the polymer substrate; and, in the case of reusable lenses, the coatings must exhibit sufficient abrasion resistance and chemical stability to withstand repeated cleanings. In the latter case, cleaning procedures would include both exposure to harsh chemical cleansing agents and to mechanical rubbing actions.

European Patent Application 93810399.1, filed Jun. 2, 1993, describes a complicated multi-step process to alter the surface of a contact lens material. The process requires a plasma treatment of the surface to generate surface free radicals, which are reacted with oxygen to form hydroperoxy groups, to which are graft polymerized an ethylenically unsaturated monomer plus cross-linking agent, followed by a solution extraction period to remove unreacted monomers. This complex process requires the presence of inhibition agents during the monomer coupling reactions to prevent the homopolymerization of the ethylene monomers by free radicals generated during the thermal decomposition of the hydroperoxy groups.

The plasma deposition of triethylene glycol monoallyl ether is reported in the German patent application DE19548152.6. Although it did not deal with contact lenses, it centered on surface modifications to reduce the adsorption of biological compounds. Coatings of such type would be useful in reducing non-specific protein adsorption on certain biosensor surfaces. In this work, substrates for coating were located outside the plasma discharge zone and exceptionally low RF power densities were employed in an attempt to minimize fragmentation of the polyethylene oxide units present in this monomer. Not unexpectedly, coatings deposited in the relatively non-energetic region upstream of the plasma discharge and outside the luminous discharge zone were only weakly attached to the underlying substrates. Another problem encountered in this work was the low volatility of the monomer. This resulted in a requirement for monomer heating to provide sufficient vapor for the plasma deposition process. However, even with heating, the vapor pressures obtainable without initiating thermal decomposition of the monomer were too low to provide any sort of flow rate and/or reactor pressure controllability. Additionally, the unusually low vapor pressure resulted in exceptionally low film deposition rates with accompanying film non-uniformity. The coatings obtained were not tested for adhesion under flow conditions, nor were they subjected to any abrasive cleaning or rubbing actions. Simple soaking of the coating substrates in distilled water for relatively short periods (e.g., less than 48 hours) resulted in measurable changes in the chemical compositions of the coatings as revealed by XPS surface analysis of these coatings before and after the simple water immersion test.

U.S. Pat. Nos. 3,008,920 and 3,070,573 reveal the use of plasma surface treatments to generate free radicals for subsequent peroxy group formation followed by the grafting of vinylic monomers to the polymer substrate. The control of the depth uniformity and density of the grafted coatings is a difficult problem encountered in these grafting experiments.

PCT/US90/05032 (Int. Publication #WO91/04283) discloses increasing the wettability of polymeric contact lens materials synthesized from specific hydroxy acrylic units and vinylic siloxane monomers by grafting other molecules to the surface. The only examples of the proposed grafting procedure described in this patent involve attachment of specific polyols by wet chemical procedures, but this patent does suggest that hydroxy acrylic units may be grafted to the specific hydroxy acrylic/siloxane polymeric materials by radiation methods. Additionally, radiation induced attachment by gaseous hydroxyl acrylic units was described in U.S. Pat. No. 4,143,949 as a means of improving surface hydrophilic character.

U.S. Pat. No. 4,143,949 discloses a process for putting a hydrophilic coating on a hydrophoic contact lens. The polymerization is achieved by subjecting a monomer, in gaseous state, to the influence of electromagnetic energy, of a frequency and power sufficient to cause an electrodeless glow discharge of the monomer vapor.

U.S. Pat. No. 4,693,799 describes a process for producing a plasma polymerized film by pulse discharging. The process comprises forming a plasma polymerized film on the surface of a substrate placed in a reaction zone by subjecting an organic compound containing gas to plasma polymerization utilizing low temperature plasma formed by pulse discharging, in which the time of non-discharging condition is at least 1 msec, and the voltage rise time for gas breakdown is not longer than 100 msec. Specifically, the patent disclosed a process employing an alternating current ("AC") electrical discharge operated in a pulsed mode to provide films having small coefficients of friction and high lubricity for use on magnetic tapes and discs. Although various experimental sets were carried out at different AC frequencies (from 2 to 2 Khz), all experiments within a given set were reportedly conducted at fixed plasma on to plasma off times. However, it provides no mention of the film compositional control available via changes in the ratio of plasma on to plasma off times during pulsed plasma polymerization of an organic monomer; nor is any mention made of the adhesion of the deposited films with respect to soaking or abrasive cleaning actions.

U.S. Pat. Nos. 3,854,982 and 3,916,033 describe the use of liquid coating techniques to improve the wettability of contact lens polymers. In these procedures free radical polymerizable precursors, including hydroxy alkyl methacrylates, are attached to contact lenses by exposure to high energy radiation. However, these solution attachment processes provide poor control of the film thickness and these films exhibit poor abrasion resistance, particularly when attached to polysilicone substrates.

The direct plasma treatment to improve the wettability of contact lenses is described in U.S. Pat. No. 3,925,178 in which an electrical or radio frequency discharge in water vapor is employed for that purpose. This non-coating treatment results in a relatively unstable hydrophilic surface in which the wettability of the contact lens substrate decreases rapidly in time.

U.S. Pat. No. 5,153,072 describes a method of controlling the chemical structure of polymeric films by plasma deposition and films produced thereby. The focus of this invention involves controlling the temperature of the substrate and the reactor so as to create a temperature differential between the substrate and reactor such that the precursor molecules are preferentially adsorbed or condensed on the substrate either during plasma deposition or between plasma deposition steps.

Yasuda et al., "Some Aspects of Plasma Polymerization Investigated by Pulsed R.F. Discharge," *Journal of Polymer Science: Polymer Chemistry Edition*, Vol. 15, pp. 81–97 (1977), discloses the polymerization of organic compounds in glow discharge (plasma polymerization) by using pulsed RF discharge (100 microsec. on, and 900 microsec off). The effect of pulsed discharge on polymer deposition rate, pressure change in plasma, ESR signals of free spins in both plasma polymer and substrate, and the contact angle of water on the plasma polymer surface were investaged for various organic compounds.

Nakajima et al., "Plasma Polymerization of Tetrafluoroethylene," *Journal of Applied Polymer Science*, Vol. 23, pp. 2627–2637 (1979), describes the plasma polymerization of tetrafluoroethylene in both continuous wave and pulsed radio frequency ("RF") discharges. They reported that both polymer deposition rates and polymer structures were essentially identical when using continuous wave and pulsed RF discharge.

Lopez et al., "Glow discharge plasma deposition of tertraethylene glycol dimethyl ether for fouling-resistant biomaterial surfaces," *Journal of Biomedical Materials Research*, Vol. 26, pp 415–439 (1992), discloses the glow discharge plasma deposition of tetraethylene glycol dimethyl ether onto glass, polytetrafluoroethylene and polyethylene. The monomer required heating, and low power to retain the ethylene oxide content of the plasma deposited coatings. As a result, no monomer flow rate controllability was available, and the films deposited at the lower RF powers exhibited low stability to even simple overnight soaking in water. The film adhesion to the polymeric substrate could be improved by carrying out the plasma deposition at higher power but this improved adhesion was achieved at the expense of loss of ethylene oxide film content and thus poorer non-fouling properties.

The need still remains for a composition which can be applied to the surface of a substrate to provide a film of coating that is uniform in thickness, pin-hole free, optically transparent in the visible region of the magnetic spectrum, permeable to oxygen, biologically non-fouling, relatively abrasive resistant, and wettable (hydrophilic).

SUMMARY

The present invention provides a device comprising a substrate and a coating composition, the coating composition being formed by the gas phase or plasma polymerization of a gas comprising at least one organic compound or monomer, the organic compound having the following structure:

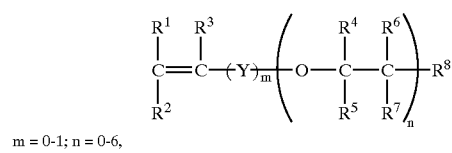

m = 0-1; n = 0-6, where Y represents C=O;

$R^1$, $R^2$, $R^3$, $R^4$, $R^5$, $R^6$ and $R^7$ each independently represents:
H,
OH,
halogen,
$C_1$–$C_4$ alkyl,
$C_1$–$C_4$ alkene,
$C_1$–$C_4$ diene, $C_1$–$C_4$ alkyne,
$C_1$–$C_4$ alkoxy, or
$C_1$–$C_4$ alkyl halide; and $R^8$ represents:
H,
halogen,
$C_1$–$C_4$ alkyl,
$C_1$–$C_4$ alkene,
$C_1$–$C_4$ diene,
$C_1$–$C_4$ alkyne,
$C_1$–$C_4$ alkyl halide,
$C_1$–$C_4$ aldehyde,
$C_1$–$C_4$ ketone,
$C_1$–$C_4$ epoxide,
$C_1$–$C_4$ carboxylic acid,
$C_1$–$C_4$ ester,
—CH=CHR$^9$, where $R^9$ is H, halogen, $C_1$–$C_4$ alkyl, $C_1$–$C_4$ alkyl halide, $C_1$–$C_4$ aldehyde, $C_1$–$C_4$ ketone, $C_1$–$C_4$ alkoxyl, $C_1$–$C_4$ epoxide, $C_1$–$C_4$ carboxylic acid, or $C_1$–$C_4$ ester, or
—OR$^{10}$, where $R^{10}$ is H, halogen, $C_1$–$C_4$ alkyl, $C_1$–$C_4$ alkene, $C_1$–$C_4$ diene, $C_1$–$C_4$ alkyne, $C_1$–$C_4$ alkyl halide, $C_1$–$C_4$ aldehyde, $C_1$–$C_4$ ketone, $C_1$–$C_4$ epoxide, $C_1$–$C_4$ carboxylic acid, or $C_1$–$C_4$ ester.

The polymerization of the present invention can be carried out using a pulsed discharge having a duty cycle of less than about 1/5, in which the pulse-off time is less than about 2000 msec and the pulse-on time is less than about 100 msec. The duty cycle can also be varied, thus the coating composition can be gradient layered accordingly.

The compound generally has low molecular weight, one or more ether linkages and at least one unsaturated carbon-carbon bond.

The devices of this invention have coating compositions which are uniform in thickness, pin-hole free, optically transparent in the visible region of the magnetic spectrum, permeable to oxygen, abrasive resistant, wettable and biologically non-fouling; therefore, making it possible to use substrates which, except for their surface characteristics, are well suited for their intended uses. In the specific case of contact or interocular lenses, particularly contact lenses, substrates which are not wettable by the tear fluid, which are subject to rapid biological fouling, and/or have surface energies which are too low can be made useful when coated with the coating compositions of this invention.

The coatings of the present invention are deposited on the surface of a solid substrate via plasma polymerization of at least one selected monomer. The plasma deposition of the present invention is achieved by either continuous wave ("CW") or pulsed plasmas. In the pulsed mode, the deposition is carried out of a fixed plasma duty cycle or, alternately, using a variable duty cycle pulsed plasma deposition.

DETAILED DESCRIPTION

Figure 1:
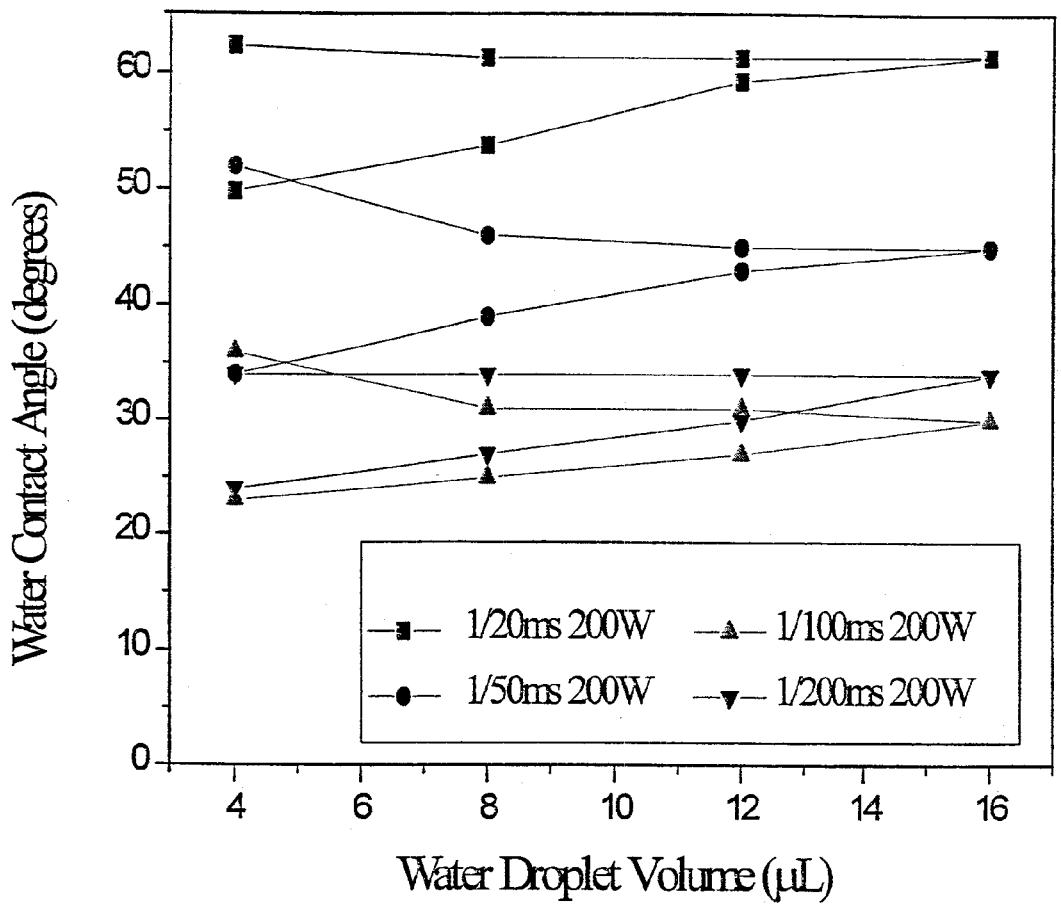
FIG. 1 is an illustration of the variation in coating wettability with changes in RF duty cycles employed during deposition, while all other plasma reaction variables were being held constant.

The devices of this invention comprise non-fouling coating compositions. The coating compositions provide surfaces which are uniform, pin-hole free, wettable, devoid of extractables, and chemically stable. Further, the coatings exhibit excellent optical transparency in the visible region of the electromagnetic spectrum, are oxygen permeable, and are abrasion resistant. These are desirable characteristics particularly for biomedical devices, such as stents, implants, catheters, etc., and particularly for contact or interoccular lenses. The coating of the present invention is also suitable for surface coating of magnetic recording media, magnetic tapes, magnetic discs, cell cultivation bed, carriers for diagnostic reagents, biosensors, and artificial organs, such as artificial blood vessels, artificial bones, and others.

The substrates for the devices of this invention can comprise polymers, plastic, ceramics, glass, silanized glass, fabrics, paper, metals, silanized metals, silicon, carbon, silicones and hydrogels. Some of the more preferred materials include those that are likely to be used for biomedical devices, such as silicone and silicone containing compositions, (mixed blends and copolymers), polyurethanes, and hydrogels, and mixtures of these materials. The most preferred substrate materials are those polymers used to make contact lenses, which do not support a stable tear film on the surface, such as silicones, silicone mixed blends, alkoxylated methyl glucosides, silicone hydrogels, polyurethane-silicone hydrogels, and polysulfones. Illustrative silicones are polydimethylsiloxane polydimethyl-co-vinylmethylsiloxane, silicone rubbers described in U.S. Pat. No. 3,228,741, silicone blends such as those described in U.S. Pat. No. 3,341,490, and silicone compositions such as described in U.S. Pat. No. 3,518,324. Useful silicone materials are the cross linked polysiloxanes obtained by cross linking siloxane prepolymers by means of hydrosilylation, cocondensation and by free radical mechanisms. Particularly suitable substrate materials are organopolysilioxane polymer mixtures which readily undergo hydrosilylation. Such prepolymers will comprise vinyl radicals and hydride radicals which serve as crosslinking sites during chain extension and crosslinking reaction and are of the general formulation comprising polydihydrocarbyl-co-vinylhydrocarbylsiloxane and polydihydrocarbyl-co-hydrocarbylhydrogensiloxanes wherein the hydrocarbyl radicals are monovalent hydrocarbon radicals such as alkyl radicals having 1–7 carbon atoms, such as, methyl, ethyl, propyl, butyl, pentyl, hexyl and heptyl; aryl radicals, such as phenyl, tolyl, xylyl, biphenyl; haloaryl, such as chlorophenyl and cycloalkyl radicals such as cyclopentyl, cyclohexyl, etc. The more preferred materials are silicone hydrogels, particularly silicone-hydrogels formed from monomer mixtures comprising an acrylic-capped polysiloxane prepolymer, a bulky polysiloxanylalkyl (meth)acrylate monomer and hydrophilic monomers as described in U.S. Pat. Nos. 5,387,632; 5,358,995; 4,954,586; 5,023,305; 5,034,461; 4,343,927; and 4,780,515. Other preferred substrate materials comprise cyclic polyols of alkoxylated glucose or sucrose like those described in 5,196,458 and 5,304,584, and U.S. patent application Ser. No. 08/712,657, filed Sep. 13, 1996. All of the patents cited above are incorporated herein by reference.

The preferred coating compositions comprise gas phase deposited low molecular weight, high volatility organic compounds containing one or more ether linkages. Preferably, the molecules contain at least one unsaturated carbon-carbon bond in the molecule to assist in achieving polymerization, particularly under low energy gas-phase deposition methods. The groups having unsaturated carbon-carbon bonds are preferably vinyl compounds. The coating compositions are stable, and adherent to a wide range of substrates while maintaining maximum integrity of the ether linkages present in these monomers. The weight average molecular weights of the compounds are preferably less than 400, more preferably less than 300, and most preferably less than 200.

The preferred coating compositions are formed by the gas phase deposition and polymerization of a linear or branched organic compound or monomer having the following structure:

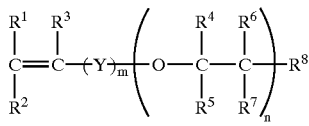

m = 0-1; n = 0-6, where Y represents C=O;

$R^1$, $R^2$, $R^3$, $R^4$, $R^5$, $R^6$ and $R^7$ each independently represents:

H,
OH,
halogen,
$C_1$–$C_4$ alkyl,
$C_1$–$C_4$ alkene,
$C_1$–$C_4$ diene,
$C_1$–$C_4$ alkyne,
$C_1$–$C_4$ alkoxy, or
$C_1$–$C_4$ alkyl halide; and $R^8$ represents:

H,
halogen,
$C_1$–$C_4$ alkyl,
$C_1$–$C_4$ alkene,
$C_1$–$C_4$ diene,
$C_1$–$C_4$ alkyne,
$C_1$–$C_4$ alkyl halide,
$C_1$–$C_4$ aldehyde,
$C_1$–$C_4$ ketone,
$C_1$–$C_4$ epoxide,
$C_1$–$C_4$ carboxylic acid,
$C_1$–$C_4$ ester,
—CH=CHR$^9$, where $R^9$ is H, halogen, $C_1$–$C_4$ alkyl, $C_1$–$C_4$ alkyl halide, $C_1$–$C_4$ aldehyde, $C_1$–$C_4$ ketone, $C_1$–$C_4$ alkoxyl, $C_1$–$C_4$ epoxide, $C_1$–$C_4$ carboxylic acid, or $C_1$–$C_4$ ester, or
—OR$^{10}$, where $R^{10}$ is H, halogen, $C_1$–$C_4$ alkyl, $C_1$–$C_4$ alkene, $C_1$–$C_4$ diene, $C_1$–$C_4$ alkyne, $C_1$–$C_4$ alkyl halide, $C_1$–$C_4$ aldehyde, $C_1$–$C_4$ ketone, $C_1$–$C_4$ epoxide, $C_1$–$C_4$ carboxylic acid, or $C_1$–$C_4$ ester.

Examples of usable organic compounds include the following structures:

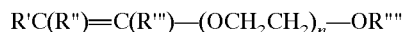
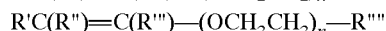
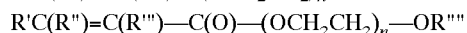
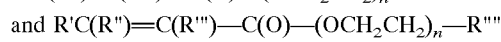

where R', R", R'", and R"" independently represent H, a linear or branched alkyl having 1 to 4 carbons; preferably methyl or H; more preferably H; and n is 1 to 6; preferably 1 to 5; more preferably 2 or 3. For specifically preferred monomers having the above structural formulas R', R", R'", and R"" are H; or R', R", R'" are H, and R"" is $CH_3$; and n is 2 or 3, more preferably 2.

Example of more specific usable organic compounds include:

Other examples of usable organic compounds in the coating composition of this invention include:

| | |
|---|---|
| di(ethylene glycol) divinyl ether | $H_2C$=CHOCH$_2$CH$_2$)$_2$O |
| di(ethylene glycol) vinyl ether | $H_2C$=CH(OCH$_2$CH$_2$)$_2$OH |
| di(ethytene glycol) methyl vinyl ether | $H_2C$=CH(OCH$_2$CH$_2$)$_2$OCH$_3$ |
| di(ethylene glycol) diacrylate | ($H_2C$=CHCO$_2$CH$_2$CH$_2$)$_2$O |
| di(ethylene glycol) ethyl ether acrylate | $H_2C$=CHC(O)(OCH$_2$CH$_2$)$_2$OC$_2$H$_5$ |
| trimethylolpropane diallyl ether | $C_2H_5$C(CH$_2$OCH$_2$CH=CH$_2$)$_2$CH$_2$OH |
| tetra(ethylene glycol) propyl ether methacrylate | $H_2C$=C(CH$_3$)CO$_2$(OCH$_2$CH$_2$)$_4$CH$_2$CH$_2$CH$_3$ |
| hexa(ethylene glycol) methyl ether methacrylate | $H_2C$=C(CH$_3$)CO$_2$(OCH$_2$CH$_2$)$_6$CH$_3$ |

The more preferred organic compounds include di(ethylene glycol) divinyl ether, di(ethylene glycol) methyl vinyl ether, di(ethylene glycol) ethyl ether acrylate, and trimethylolpropane diallyl ether. The most preferred compound is di(ethylene glycol) vinyl ether.

The coating compositions can comprise the polymerization of substantially a single organic compound or of a mixture of organic compounds with or without the addition of cross-linking agents. The single and the mixture of organic compounds preferably are selected from the organic compounds described above.

The selection of compounds and method of application of the compounds to the surface of the substrate preferably provide a coating composition in which the outermost layer of the coating has a ratio of carbon-oxygen bonds to carbon-carbon bonds of greater than 1:1, more preferably greater than 1.5:1, and most preferably greater than 2:1, even more preferred is greater than 2.5:1. The coating compositions having a higher ratio of carbon-oxygen bonds to carbon-carbon bonds are preferred, because of improved non-fouling and higher wettability characteristics.

One method for depositing the coating compositions on the substrates is by gas phase deposition, because it provides uniform coating compositions. Gas phase deposition means by any method the gaseous monomers are attached to the solid substrate as a surface coating. Gas phase depositions include plasma and photochemical induced polymerizations. Plasma induced polymerizations or plasma depositions are polymerizations due to the generations of free radicals caused by passing an electrical discharge through a gas. The electrical discharge can be caused by high voltage methods, either alternating current ("AC") or direct current ("DC"), or by electromagnetic methods, such as, radio frequency ("RF") and microwave. Alternatively, the coating process can be carried out using photochemical induced polymerizations as provided by direct absorption of photons of sufficient energy to create free radicals and/or electronically excited species capable of initiation of the polymerization process.

One preferred method of one-step gas phase deposition is by plasma polymerization, particularly radio frequency plasma polymerization, in which the coating is deposited on the surface of the substrate via direct monomer polymerization. This process will be described herein. It is more fully described in U. S. patent application Ser. No. 08/632,935, incorporated herein by reference. Additional descriptions can be found in Panchalingam et al., "Molecular Surface Tailoring of Biomaterials Via Pulsed RF Plasma Discharges," *J.Biomater. Sci. Polymer Edn.*, Vol. 5, pp. 131–145 (1993), and Panchalingam et al, "Molecular Tailoring of Surfaces Via Pulsed RF Plasma Depositions," *Journal of Applied Science: Applied Polymer Symposium*, 54, 123–141 (1994), incorporated herein by reference. In this method, coatings are deposited on solid substrates via plasma polymerization of selected monomers under controlled conditions. The plasma is driven by RF radiation using coaxial external RF electrodes located around the exterior of a cylindrical reactor. Substrates to be coated are preferably located in the reactor between the RF electrodes; however, substrates can be located either before or after the electrodes. The reactor is evacuated to background pressure using a rotary vacuum pump. A fine metering valve is opened to permit vapor of the monomer (or monomer mixtures) to enter the reactor. The pressure and flow rate of the monomer through the reactor is controlled by adjustments of the metering valve and a butterfly control valve (connected to a pressure controller) located downstream of the reactor. In general, the monomer reactor pressures employed range from approximately 50 to 200 mili-torr, although values outside this range can also be utilized. It is preferred that the compounds have sufficiently high vapor pressures so that the compounds do not have to be heated above room temperature (from about 20 to about 25° C.) to vaporize the compounds. Although the electrodes are located exterior to the reactor, the process of the invention works equally well for electrodes located inside the reactor (i.e. a capacitively coupled system).

The chemical composition of a film obtained during plasma deposition is a strong function of the plasma variables employed, particularly the RF power used to initiate the polymerization processes. It is preferred to operate the plasma process under pulsed conditions, compared to continuous wave ("CW") operation, because it is possible to employ reasonably large peak powers during the plasma on initiation step while maintaining a low average power over the course of the coating process. Pulsing means that the power to produce the plasma is turned on and off The average power under pulsing is defined as:

$$\text{Average Power} = \frac{\text{plasma-on time}}{\text{plasma-on time} + \text{plasma-off time}} \times \text{Peak Power}$$

For example, a plasma deposition carried out at a RF duty cycle of 10 msec on and 200 msec off and a peak power of 25 watts corresponds to an average power of 1.2 watts. The Peak Power is preferably between about 10 and about 300 watts.

The formal definition of duty cycle is defined as the ratio of the plasma on time (i.e. discharge time) to a sum of the plasma-on time and the plasma-off time (i.e. non-discharge time), as represented below:

$$\text{Duty cycle} = \frac{\text{plasma-on time}}{\text{plasma-on time} + \text{plasma-off time}}$$

However, for convenience, the plasma on to plasma off times are frequently cited herein as a simple ratio of on to off time, both times employing the same scale (i.e. milliseconds or microseconds).

The workable range of duty cycle is less than about $\frac{1}{5}$, the preferred range is between about $\frac{1}{10}$ and about $\frac{1}{1000}$, and the more preferred range is between about $\frac{1}{10}$ and about $\frac{1}{30}$. The plasma-on time should be larger than about 1 $\mu$sec, preferably in the range of between about 10 $\mu$sec and about 100 msec, and more preferably in the range of between about 100 $\mu$sec and about 10 msec. The plasma off time, i.e. the non-discharge time, should be larger than about 4 $\mu$sec, preferably in the range of between about 100 $\mu$sec and 2000 msec, and more preferably in the range of between about 200 $\mu$sec and about 100 msec. The total deposition time varies depending on the monomer and the conditions used. Typically, the deposition time can vary from about 0.5 min to about 3 hours.

Pulsed plasma deposition permits use of relatively high peak powers while simultaneously maintaining relatively low average powers which provides for the retention of monomer functional groups. Coating compositions deposited under low average power pulsed conditions tend to be more adhesive to a given substrate when compared to films deposited at the same average power but under CW operation. For a given average power, the momentary high peak power available under pulsed conditions apparently assists in obtaining a stronger grafting of the film to the substrate than that obtained under the same average power CW conditions.

For a given RF peak power, an increased retention of the ether content (C—O functionality) of the plasma generated coating is observed as the plasma duty cycle is reduced when working with a given monomer. Alternatively, the chemistry of the coating composition can be varied under pulsed conditions by working at a single plasma duty cycle but varying peak powers. There is an increased incorporation of C—O functionality in coating compositions as the peak power is decreased. Surprisingly, the plasma generated film composition can be varied by changing the plasma on to plasma off pulse widths, at a fixed ratio of plasma on to plasma off times and at a fixed RF peak power. Although the film deposition mode described is one of RF plasma polymerization, those familiar in the art will recognize that other polymerization methods (e.g., microwave plasmas, photo-polymerization, ionizing radiation, electrical discharges, etc.) could also be adapted for this purpose.

The chemical composition of the films of this invention can be varied during pulsed plasma deposition, by varying the peak power and/or the duration of the plasma on and plasma off pulse widths. This excellent film chemistry controllability is achieved without recourse to modulating the temperature of the substrate during the actual coating process. To produce a coating composition with the preferred ratio of C—O functionality to C—C functionality, it is preferred that the average power of the pulsed plasma deposition is less than 100 watts, more preferably less than 40 watts, most preferably less than 10 watts. The highest ratios of C—O functionality to C—C functionality can be obtained when the average power is 1 watt and less which provides the most non-fouling and wettable coating compositions.

However, as those skilled in the art will recognize, the actual effect of peak power input on film composition is dependent on the reactor volume (i.e. power density). In the present invention, the reactor volume is approximately 2 liters. Obviously, if a smaller reactor were employed, the same film compositioned changes reported herein would be achieved at lower peak power inputs. Other reaction variables which would influence peak power inputs are reactor pressure and monomer(s) flow rates. If larger reactor volumes were employed, the same film compositional variations could be achieved using higher power input.

The use of lower average power conditions increases the presence of functional groups, e.g. ether units, in the coatings, but the less energetic deposition conditions at lower average power may result in poorer adhesion of the polymer film to the underlying substrate. Thus, the plasma coating process involves somewhat of a compromise between retention of monomer integrity in the plasma generated film and the strength of the adhesion between the coating and the solid substrate. In the case of biomedical devices and contact lenses, the adhesion and overall stability of the coating composition to the lens substrate is an extremely important consideration.

One method of applying the coating compositions to the substrate of the present invention is by pulsed plasma coupled with gradient layering. The duty cycle can be varied, thus creating variable duty cycle. The method can be used to maximize the adhesion of the coating composition and the functionalities present in the coating composition. Films deposited under low average power pulsed conditions tend to be more adhesive to a given substrate when compared to films deposited at the same average power but under CW operation. For a given average power, the momentary high peak power available under pulsed conditions assists in obtaining a stronger grafting of the film to the substrate than that obtained under the same average power CW condition. This stronger grafting under pulsed conditions is repeated with each plasma on cycle. The better grafting of the film to the substrate obtained under pulsed conditions can be even further enhanced by combining the pulsed deposition with a gradient layering technique. This method is described further in U. S. patent application Ser. No. 08/632,935, which is incorporated herein by reference. In this process, an initial high power, high plasma duty cycle is employed to graft the plasma generated coating composition tightly to the underlying substrate. The plasma duty cycle is subsequently progressively decreased in a systematic manner, with each decrease resulting in an increased retention of the C—O functionality in the coating. In this way, the successive plasma deposited films are tightly bonded to each other. The process is terminated when the exterior film layer has reached the desired composition. The succession of thin layers, each differing slightly in composition in a progressive fashion from the preceding one, results in a significantly more adhesive composite coating composition bonded to the substrate than coatings deposited without adjusting the deposition conditions under a relatively lower plasma duty cycle.

Gas-phase deposition, particularly plasma depositions, provide coating compositions of substantially uniform thickness. The thicknesses of the coating composition could be between 5 Å and 5 $\mu$m, more preferably between 50 Å and 1 $\mu$m, and most preferably between 100 Å and 0.1 $\mu$m. The uniform film thickness and controllability of the deposition method can be contrasted with thickness controllability problems encountered using previously disclosed methods. Using the RF pulsed plasma deposition provides linearity of the thickness of the coating composition with deposition time for a given plasma duty cycle and fixed monomer pressure and flow rate.

The coatings of this invention increase the hydrophilic character of the surface of the substrates, particularly with substrates that are more hydrophobic (e.g., polysiloxanes). The extent of hydrophilicity introduced during the plasma process was observed to increase as the oxygen content of the plasma generated coating compositions increased.

The wettabilities of the substrates employed were measured before and after plasma coating using both static and dynamic water contact angle measurements. In general, the coatings applied serves to increase the hydrophilic character of the surface, particularly with substrates that are more hydrophobic (e.g., polysiloxanes). The extent of hydrophilicity introduced during the plasma process was observed to increase as the oxygen content of the plasma generated films increased.

The stability of the surface wettability was examined in several ways, including exposure to aqueous solution flow and to abrasive cleaning and rubbing tests. Additional successful stability testing of the coated substrates involved autoclaving for five cycles at 121° C. for 30 minutes each cycle. The examples below include the results of these tests.

The non-fouling character of the coating compositions were measured using adsorption studies with radioactively labeled proteins, as well as by total protein assay. In general, decreases in protein adsorption were observed for coated polymer substrates as compared to uncoated polymer substrate as shown in the examples which follow.

The optical transparency of the coating compositions was measured spectrophotometrically at wavelengths ranging from 800 to 200 nm. The plasma coating compositions of the invention exhibited consistent excellent transparency over the entire region of the visible spectrum (i.e., from 780 to 380 nm) with photon absorption beginning to occur around 370 nm in the near UV region. The absorption increases sharply over the interval from 370 to 200 nm, as revealed by samples deposited on quartz plates.

The oxygen permeability was measured using the Fatt Method (Fatt, I. et al, *International Contact Lens Clinic*, 9(2), pp. 76–88 1992). In general, the oxygen permeabilities (reported as DK values) of the polymeric substrates were not measurably decreased by the presence of the plasma film on the surface.

The substrates with coating compositions of this invention are suited for contact lenses and other biomedical devices. The coating compositions exhibit good adhesion, high wettability, high oxygen permeability, and excellent transparency in the visible region of the electromagnetic spectrum when deposited on polymer substrates. The adhesion of the coating compositions to these substrates are sufficiently strong to resist delamination.

Thus the coating composition applied by a one-step and all-dry process of this invention satisfies the stringent criteria listed above to improve the biocompatibility of contact lenses. The emphasis in this invention has been placed on the contact lenses; however, those skilled in the art will recognize that the highly wettable, biologically non-fouling, transparent coatings of this invention are useful for various other applications (e.g., biomedical devices, biosensors, detectors deployed in marine environments, membranes, tissue culture growth, implants, etc.). A particularly surprising result obtained in the present study is the remarkably stable and good biologically non-fouling properties of these coatings despite the very low molecular weights of the monomers employed to form the coating compositions. This observation is contrary to many previous studies which conclude that relatively large polymeric molecules containing ether linkages are required in order to observe the non-fouling effect.

The approach of the present invention represents an unusually simple, one-step coating process which could be conveniently coupled with a plasma based sterilization procedure to provide large scale fabrication polyethyleneglycol ("PEG") modified surfaces. Additional inherent advantages of a plasma based approach would include successful surface modifications being less dependent on the composition and geometry of the solid substrates. Tetraethylene glycol dimethyl ether, $CH_3O(CH_2CH_2O)_4CH_3$, and tri(ethylene glycol) monoallyl ether, $CH_2=CHCH_2(OCH_2CH)_3OH$, were studied as potential monomers for plasma polymerized PEG surfaces. For example, tetraethylene glycol dimethyl ether was plasma deposited to yield surfaces with high short-term resistance to biomolecular absorption, as demonstrated with both plasma protein and cellular adsorption studies. However, simple overnight soaking of plasma coated substrates in water resulted in major chemical compositional changes as revealed by XPS analysis of surfaces before and after soaking. Similarly, plasma polymerization of tri(ethylene glycol) monoallyl ether produced coatings having good short term resistance to biofouling but poor stability towards soaking or exposure to flowing aqueous solutions. Adhesion of the plasma films to the polymeric substrates could theoretically be improved by carrying out the plasma deposition at higher power but this improved adhesion was achieved at the expense of loss of ethylene oxide film content and thus poorer non-fouling properties.

Although not wishing to be bound by any particular postulate, it is speculated that the gas phase deposition process, particularly the pulsed plasma deposition process of the present invention results in an unusually efficient stacking of ether linkages on the substrate surface thus providing a high surface density of such groups. This high surface density is, in turn, extremely effective in preventing the adsorption of biological molecules onto the surface while simultaneously creating a relatively polar environment to adsorb water molecules, thus providing high surface wettability. When the coating process is used for contact lenses, the coating composition on the contact lens substrate should provide a low water contact angle. For contact lenses, it is preferred that the coating compositions have an advancing sessile drop water contact angle of less than 85°, more preferably less than 65°, most preferably less than 45°.

EXAMPLE 1

Di(ethylene glycol) vinyl ether (EO2V) was plasma deposited on a Dacron™ polyester substrate under pulsed plasma deposition conditions using an RF on/off cycle of 10 msec on and 200 msec off at 100 W peak power. A 1000 Å thick film was deposited during the 20 minute run. X-ray photoelectron spectroscopy (XPS) analysis of this film revealed significantly more carbon atoms bonded to oxygen than to other carbon atoms. A sample prepared in this manner was then subjected to 65 hours of a constant 40 ml/min flow of phosphate buffer solution (PBS) at pH of 7.4. The sample was subsequently vacuum dried and re-analyzed by XPS. The relative concentration of C—O to C—C groups present on the surface had actually increased slightly revealing negligible surface modification during the buffer flow, indicating the durability of the coating composition.

EXAMPLE 2

A sample prepared as described in Example 1 was deposited on a silicone contact lens substrate. The advancing water contact angle was measured on the polysiloxane before and after plasma treatment. The advancing sessile drop water contact angle of 98° observed on the untreated surface had decreased to 58° after surface coating by the plasma, indicating an increased wettability due to the coating composition. Subsequent soaking of the coated sample in PBS buffer solution for several days resulted in essentially negligible change in the advancing water contact angles, indicating the durability of the coating composition. See, TABLE I. The ratio $10/200$ in TABLE I indicates 10 msec plasma-on time and 200 msec plasma-off time.

TABLE I

Contact Angle Variation for EO2V Films on Silicone Contact Lenses as a Function of Soaking Time in PBS Buffer Solution

| Coating Condition | Fresh Film | 5 hrs | 10 hrs | 48 hrs | 96 hrs | 240 hrs |
|---|---|---|---|---|---|---|
| 10/200, 100w, 15 min | 58 | 60 | 66 | 63 | 60 | 60 |
| 10/200, 100w, 30 min | 58 | 62 | 58 | 62 | 60 | 60 |

EXAMPLE 3

Figure 2:
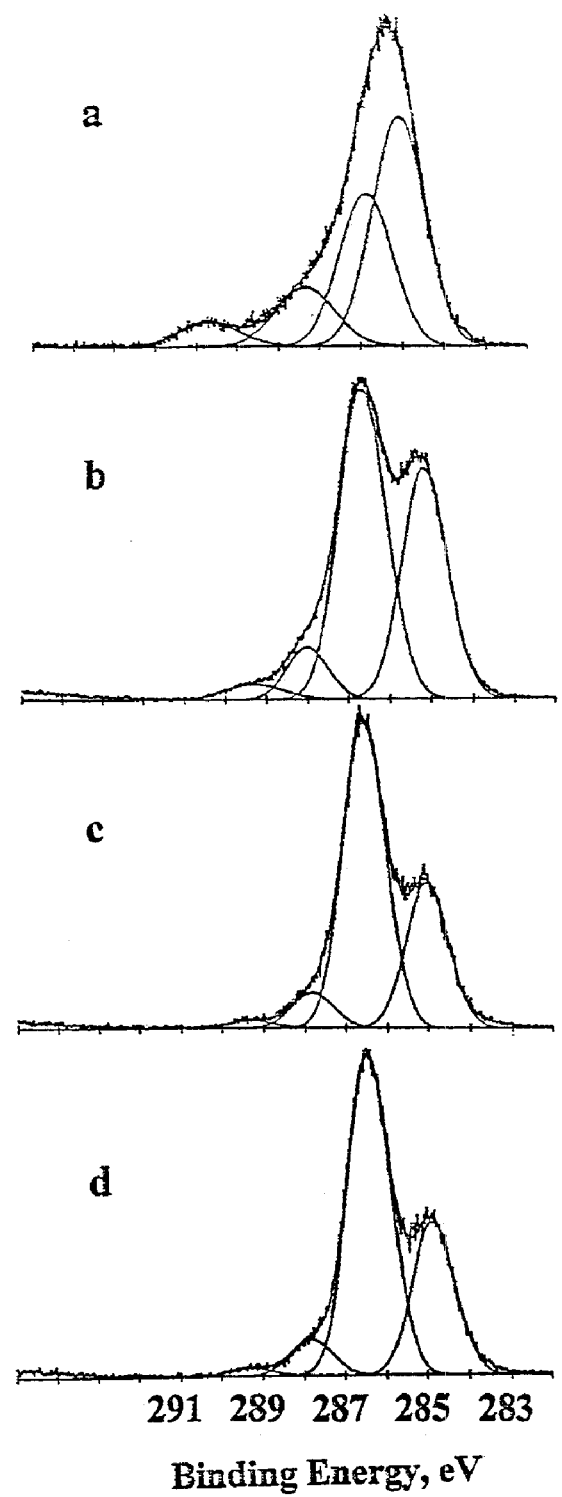
FIGS. 2(a–d) are illustrations of the variation in coating composition with changes in RF duty cycles employed during deposition of plasma polymerized EO2V film at 200 watts, while all other plasma reaction variables were being held constant. The numerator given below denotes the plasma-on time, and the denominator given below denotes the plasma-off time, both in the unit of msec. High resolution C (1s) XPS spectra are shown for films deposited at RF on/off ratio (in msec) of: (a) 1/20; (b) 1/50; (c) 1/100; and (d) 1/200.

Samples were prepared as described in Example 1 on a polyethylene substrate, but at various plasma on/off cycles of on-time in msec/off-time in msec of $1/20$, $1/50$, $1/100$, and $1/200$ at a peak power of 200 watts. Analysis of these films by water contact angle goniometry revealed progressively lower advancing water contact angles corresponding to lower RF plasma duty cycles employed during the coating procedure. (FIG. 1) The increased wettability observed with decreasing average power during film formation is correlated with high resolution C (1s) XPS spectra of these films which show increasing C—O versus C—C film content with decreasing RF duty cycle employed during film formation. (FIGS. 2(a–d)).

Figure 3:
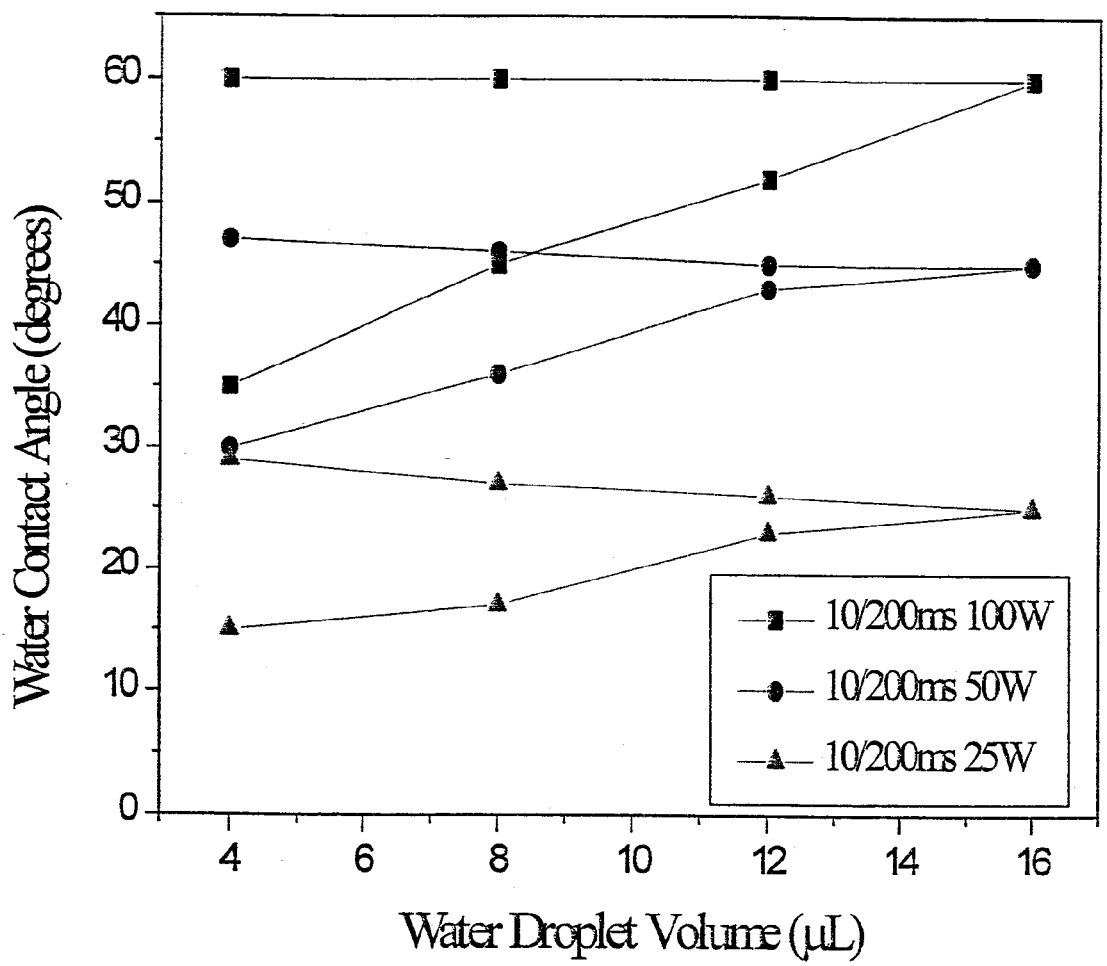
FIG. 3 is an illustration of the variation in coating wettability with changes in RF peak power employed during deposition, at a constant plasma on/off ratio of 10/200 msec, all other plasma reaction variables were held constant.

Another set of samples were prepared as described in Example 1 on a Dacron™ substrate but at various plasma peak power of 100 watts, 50 watts, 25 watts and 10 watts and at a cycle of 10 msec on and 200 msec off. Analysis of these films by water contact angle goniometry revealed progressively lower advancing water contact angles corresponding to lower RF plasma peak power employed during the coating procedure. (FIG. 3). The increased wettability observed with decreasing average plasma energy correlated with XPS analysis of these films which showed increasing C—O versus C—C film content with decreasing RF peak power employed during film formation.

EXAMPLE 4

The monomer $CH_2=CH-(OCH_2CH_2)_2OCH_3$ (Methyl EO2V) was plasma deposited on a polysiloxane substrate using the same RF duty cycle and peak power employed in Example 1. The resulting film revealed slightly higher C—O content relative to C—C bonds than obtained in Example 1. Additionally, these films exhibited an advancing water contact angle which was approximately 5° less (i.e., more hydrophilic) than that obtained in Example 2.

EXAMPLE 5

A coating was prepared from the monomer di(ethylene glycol) divinyl ether $[H_2C=CHOCH_2CH_2)_2O]$ using the same plasma deposition conditions employed in Examples 1 and 4. The advancing water contact angle for this sample was virtually identical to that obtained for the methoxy compound of Example 4. Both the methoxy and divinyl samples of Examples 4 and 5 revealed less hysteresis in terms of advancing versus receding water contact angles than observed for the sample of Example 2, indicating that the surface molecules are less mobile, and therefore less likely to foul. Further, the contact angles indicate that the surfaces are wettable.

EXAMPLE 6

A sample was prepared in which the monomer of Example 1 was plasma deposited onto a Dacron™ sample using an RF on/off cycle of 10 msec on and 200 msec off and a peak power of 50 watts. Protein adsorption using $^{125}$I-labeled albumin and fibrinogen was conducted using uncoated and plasma coated Dacron™ samples. The protein adsorption on the coated samples was dramatically reduced (i.e., by a factor in excess of 20) when compared to adsorption on the uncoated Dacron™ control. The differences were particularly acute in contrasting protein retained on these surfaces after gently washing with 1% sodium-dodecyl sulfate (SDS) solution. The retained protein was barely detectable on the plasma treated surfaces, being several orders of magnitude less than that retained on the uncoated Dacron™ controls. This example indicates both the durability and non-fouling properties of the coating composition of the invention.

Another sample was prepared in which the monomer of Example 1 was plasma deposited onto a Dacron™ sample using an RF duty cycle of 10 msec on and 50 msec off and a peak power of 100 watts. The protein adsorption on the coated samples was increased (i.e. by a factor of about 1.2) when compared to adsorption on the uncoated Dacron™ control. This example shows that the non-fouling properties of coatings made at high RF duty cycle (⅕) are not as desirable as those coatings made at low RF duty cycle.

EXAMPLE 7

Samples were prepared as described in Example 1. These samples were then subjected to abrasive cleaning processes using standard commercial contact lens cleansers following the lens cleaning instructions provided by the manufacturers. Negligible changes in surface wetting were observed in comparing coated samples before and after the abrasive cleaning processes as measured by the repeated dynamic water content angle method.

EXAMPLE 8

Samples were prepared as described in Example 1 and were deposited on a silicone contact lens. These samples were subjected to water vapor autoclaving at 121° C. for 5 successive sterilizing cycles, each of 30 minutes duration. Negligible changes in the surface wettabilities were observed in comparing samples before and after autoclaving, indicating the durability of the coating compositions.

EXAMPLE 9

Silicone contact lens substrates were coated using a gradient layering technique. In this process an initially high duty cycle plasma deposition was carried out for 30 seconds at a power of 100 watts and plasma on/off cycle of 10 msec on and 20 msec off Subsequently the plasma off time was increased sequentially to values of 50, 100, 150 and 200 msec. At each on/off cycle, the plasma deposition was operated for several minutes with the final $^{10}/_{200}$ deposition being carried out for 5 minutes. The resulting gradient layered film structure exhibited exceptional abrasion resistance and stability towards long term (i.e., 15 days) soaking under rapid (40 ml/min) flow conditions in PBS buffer at a pH of 7.2. XPS (X-ray Photoelectron Spectroscopy) analysis of the surface composition of this layered structure revealed a high resolution C(1s) spectrum having essentially the same composition as that observed from a direct 10 msec plasma on and 200 msec plasma off deposition at 100 watts peak power.

EXAMPLE 10

The increased wettability of substrates having the coating composition of this invention are shown by this example.

Water contact angle measurements were measured using both static (sessile drop) and dynamic (modified Wilhelmy plate) methods for coated and uncoated substrates. Static measurements were made using distilled water and a Rame'-Hart goniometer. Dynamic measurements were made using substrates immersed in succession in three solutions, namely: saline; protein; and then again in saline. The protein solution contained a mixture of albumen, lysozyme and immunoglobin. Advancing and receding contact angles were measured under both static and dynamic conditions. In the static experiments, the advancing contact angles were measured at 4 μL volume intervals as the water droplet was increased from 4 to 16 μL. Receding angles were recorded as the droplet size was reduced from 16 to 4 μL, again at 4 μL intervals. The dynamic measurements were each repeated four times as the sample was cycled up and down, with the average value being recorded for these four measurements.

Hydrophobic polymeric substrates (e.g. polyethylene; polyethylene terephthalate) having static water contact angles in excess of 85° were employed. After plasma coating with coating compositions of this invention, the wettability of the surfaces increased, evidenced by the large decreases in the water contact angles. No substrate dependence was observed in achieving the improved wettabilities.

Table II provides results of static sessile drop water contact angles observed after treatment of an initially hydrophobic polymeric substrate with plasma deposited films by plasma deposition of di(ethylene glycol) vinyl ether monomer. As show in Table II, all samples revealed a decrease in water contact angles from the uncoated substrate whose advancing angle was in excess of 85°. Also as shown in Table II, the exact extent of increased surface wettability is a function of the plasma deposition conditions, with the wettability generally increasing as the average power employed during coating was reduced.

TABLE II

STATIC CONTACT ANGLES

| Plasma Coated | RF Duty ON, msec | Cycle Times OFF, msec | Peak Power (W) | Average Power (W) | Advancing Angle | Receding Angle |
|---|---|---|---|---|---|---|
| Yes | 10 | 200 | 100 | 4.76 | 60 | 33 |
| Yes | 10 | 200 | 50 | 2.38 | 46 | 30 |
| Yes | 10 | 200 | 25 | 1.19 | 30 | 15 |
| Yes | 1 | 20 | 200 | 9.52 | 60 | 48 |
| Yes | 1 | 50 | 200 | 3.92 | 46 | 33 |
| Yes | 1 | 100 | 200 | 1.98 | 33 | 22 |
| Yes | 1 | 200 | 200 | 0.995 | 32 | 23 |
| No | | | | | >85 | |

The dynamic (i.e. modified Wilhelmy plate) contact angle measurements are listed in Table III for samples prepared by plasma deposition of di(ethylene glycol) vinyl ether as described above, using an RF on/off cycle of 10 msec on and 200 msec off and 100 watts peak power. The advancing and receding contact angles are shown for measurements in the three separate solutions, with these measurements being carried out in succession. As in the static measurements, the dynamic studies reveal consistently lower contact angles for the coated substrates with the surface wettability being appreciably higher for samples immersed in the protein containing solutions.

Overall, the water contact angle measurements illustrate the transformation of the initial hydrophobic polymer surface to a hydrophilic wettable surface as provided by the plasma deposited coatings.

TABLE III

DYNAMIC CONTACT ANGLES

| Solution | Advancing Angle | Receding Angle |
|---|---|---|
| Saline | 61 | 43 |
| Protein in Solution | 25 | 22 |
| Saline | 45 | 43 |

EXAMPLE 11

Static (sessile drop) water contact angles, both advancing and receding, were measured on polymeric substrates, plasma coated with different monomers. The monomers employed were diethylene glycol vinyl ether (EO2V), diethylene glycol methyl vinyl ether (Methyl EO2V), diethylene glycol divinyl ether (Divinyl EO2V), and diethylene glycol ethyl ether acrylate (Acrylate EO2V). These four coatings are given in the table which follows. All plasma films were deposited under the identical RF on/off cycle of 10 msec on and 200 msec off and 100 watts peak power. In each case, the uncoated hydrophobic polymeric surface (initially an advancing angle in excess of 85°) was transformed to a highly wettable hydrophilic surface by the plasma deposition. As shown in Table IV, the hydrophilicity of the resulting surfaces were relatively constant with each of these monomers, with the degree of hysteresis between advancing and receding contact angles being significantly reduced for the two monomers not terminated in —OH groups (i.e. Methyl EO2V and Divinyl EO2V).

The results obtained clearly illustrate the utility of employing the coatings of this invention to transform the surface of the substrate from hydrophobic to hydrophilic.

TABLE IV

STATIC CONTACT ANGLES

| Monomer | Advancing Angle | Receding Angle |
|---|---|---|
| EO2V | 60 | 33 |
| Methyl EO2V | 53 | 47 |
| Divinyl EO2V | 55 | 49 |
| Acrylate EO2V | 65 | 47 |

These examples show that the coating compositions of this invention can be used to provide non-fouling and hydrophilic surfaces to substrates, which have bulk properties which are well-suited for particular applications. These coatings are particularly suited for biomedical applications and in particular for contact or interoccular lenses.

The invention has been described in detail with particular reference to preferred embodiments thereof, but it will be understood that variations and modifications can be effected with the spirit and scope of the invention.

EXAMPLE 12

Figure 4:
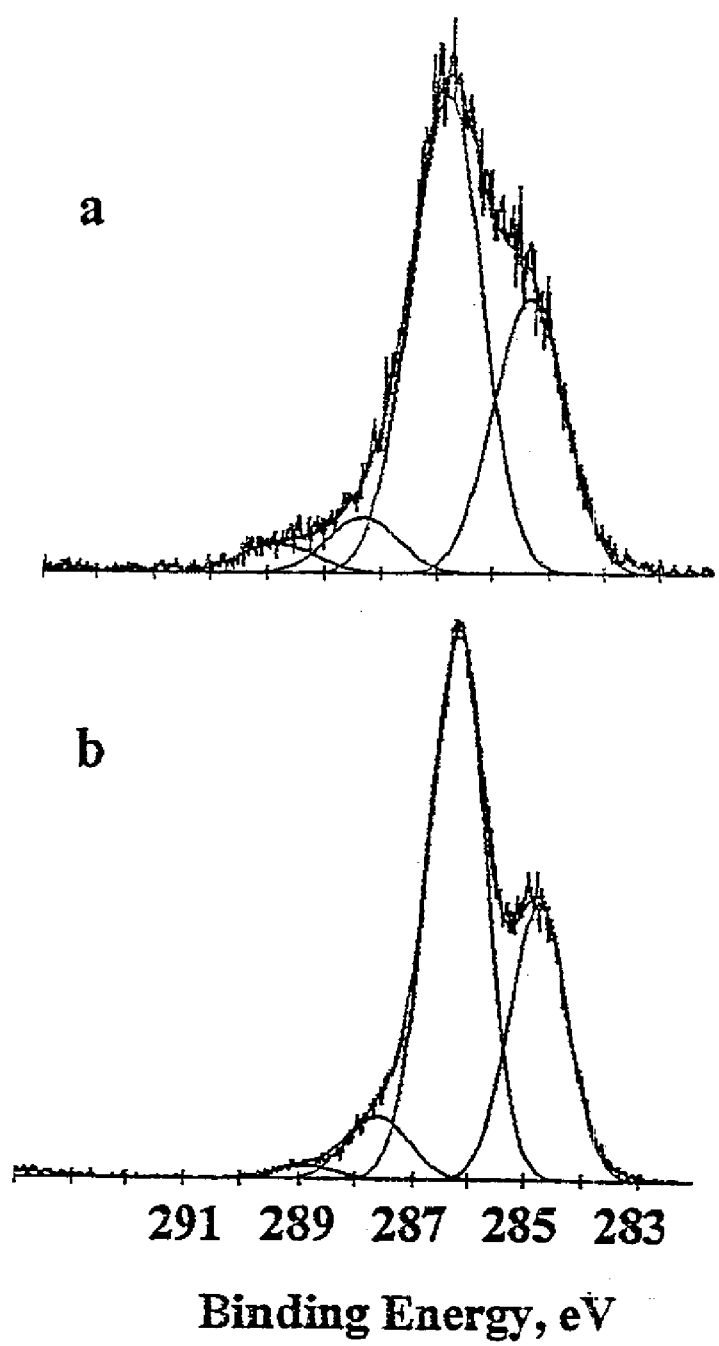
FIGS. 4(a–b) are illustrations of the stability of EO2V plasma films to prolonged exposure to air. The EO2V plasma film was deposited at a plasma-on time of 10 msec and a plasma-off time of 200 msec at 50 watts. The spectra shown are C (1s) XPS results of these films: (a) after exposure to air for 10 months; and (b) fresh film.

A sample on a silicon substrate was prepared from the monomer of Example 1 using plasma deposition conditions of an RF on/off cycle of 10 msec on and 200 msec off a peak power of 50 watts. XPS analysis of this film revealed significantly more carbon atoms bonded to oxygen than to other carbon atoms. A sample prepared in this manner was then exposed to air for 10 months for a long term stability experiment. The sample was then re-analyzed by XPS. The relative concentration of C—O to C—C groups present on the surface had actually increased slightly revealing negligible surface modification during air exposure, indicating the durability of the coating composition. (FIGS. 4(a–b)).

EXAMPLE 13

Samples were prepared as described in Example 1 on quartz substrate. Analysis of these films by UV-VIS spectrometry showed complete light transmission over the entire visible region of the electromagnetic spectrum, 380 to 800 nm.

EXAMPLE 14

Figure 5:
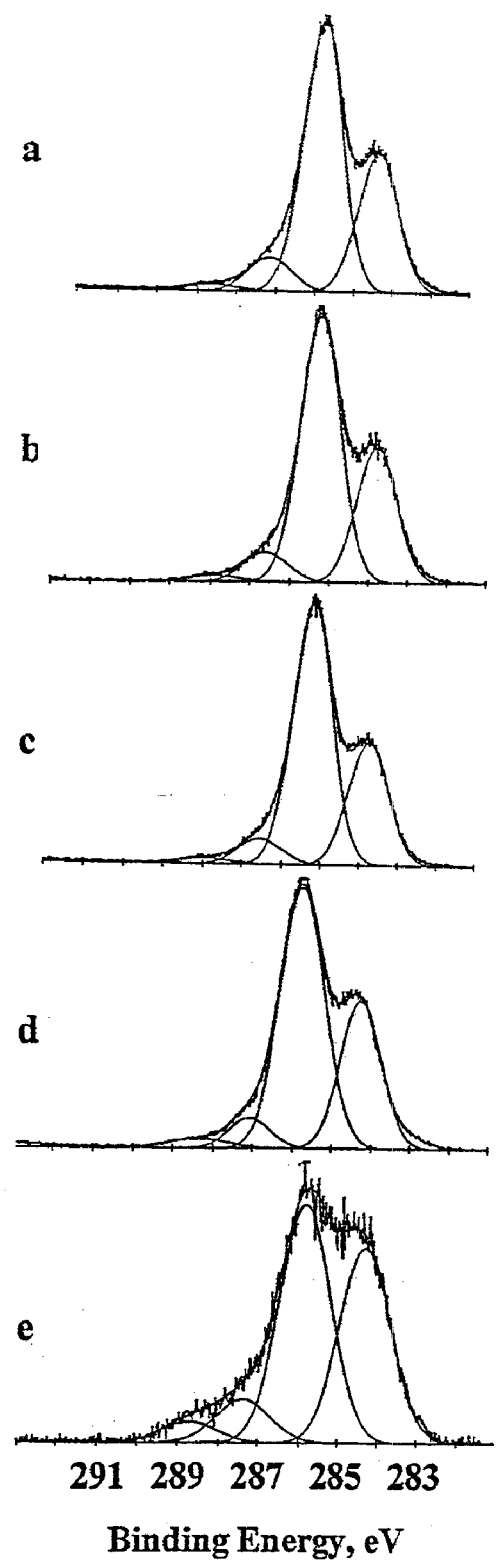
FIGS. 5(a–e) are illustrations of XPS high resolution C (1s) spectra of plasma polymerized EO2V films obtained from a series of runs carried out at a fixed plasma-on to plasma-off ratio of 1 to 20 at 50 W but with varying actual plasma-on and plasma-off pulse width: (a) 100 msec on and 2000 msec off, (b) 10 msec on and 200 msec off, (c) 1 msec on and 20 msec off, (d) 0.1 msec on and 2 msec off, and (e) 0.01 msec on and 0.2 msec off.

Samples were prepared as described in Example 1 on Dacron™ substrates at a fixed plasma-on to plasma-off ratio of 1 to 20 but with actual plasma-on and plasma-off pulse widths varying from 100 msec to 10 $\mu$sec and 2000 msec to 200 $\mu$sec, respectively. All runs were carried out at a peak power of 50 watts and at constant flow rate and reactor pressure of the EO2V monomer. XPS high resolution C(1s) spectra showed that a variation in the percent retention of the ether content of the plasma generated films was observed in these experiments with different plasma-on and plasma-off pulse widths but all runs carried out at a constant average power of 2.4 watts. (FIGS. 5(a–e)).

EXAMPLE 15

Samples are prepared as described in Example 1 using a 10 $\mu$sec plasma-on time and a 400 $\mu$sec plasma-off time. Again, highly wettable surfaces can be obtained containing high C—O bonds relative to C—C bonds, thus illustrating the production of usable films under ultrashort (i.e. microsecond) pulse times.

What is claimed:

1. A device comprising a substrate and a coating composition, said coating composition being formed by the gas phase polymerization of a gas comprising at least one organic compound, said gas phase polymerization being pulsed, having a duty cycle of less than 1/5, in which the pulse-on time is less than 100 msec and the pulse-off time is less than 2000 msec, and said organic compound having the following structure:

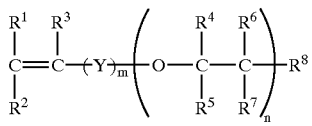

m = 0-1; n = 2-5, where Y represents C=O;
R$^1$, R$^2$, R$^3$, R$^4$, R$^5$, R$^6$ and R$^7$ each independently represents:
H,
OH,
halogen,
C$_1$-C$_4$ alkyl,
C$_1$-C$_4$ alkene,
C$_1$-C$_4$ diene,
C$_1$-C$_4$ alkoxy, or
C$_1$-C$_4$ alkyl halide; and
R$^8$ represents:
H,
halogen,
C$_1$-C$_4$ alkyl,
C$_1$-C$_4$ alkene,
C$_1$-C$_4$ diene,
C$_1$-C$_4$ alkyne,
C$_1$-C$_4$ alkyl halide,
C$_1$-C$_4$ aldehyde,
C$_1$-C$_4$ ketone,
C$_1$-C$_4$ epoxide,
C$_1$-C$_4$ carboxylic acid,
C$_1$-C$_4$ ester,
—CH=CHR$^9$, where R$^9$ is H, halogen, C$_1$-C$_4$ alkyl, C$_1$-C$_4$ alkyl halide, C$_1$-C$_4$ aldehyde, C$_1$-C$_4$ ketone, C$_1$-C$_4$ alkoxy, C$_1$-C$_4$ epoxide, C$_1$-C$_4$ carboxylic acid, or C$_1$-C$_4$ ester, or
—OR$^{10}$, where R$^{10}$ is H, halogen, C$_1$-C$_4$ alkyl, C$_1$-C$_4$ alkene, C$_1$-C$_4$ diene, C$_1$-C$_4$ alkyne, C$_1$-C$_4$ alkyl halide, C$_1$-C$_4$ aldehyde, C$_1$-C$_4$ketone, C$_1$-C$_4$ epoxide, C$_1$-C$_4$ carboxylic acid, or C$_1$-C$_4$ ester.

2. The device of claim 1, wherein said organic compound is selected from the group consisting of:
R'C(R")=C(R''')—(OCH$_2$CH$_2$)$_n$—OR'''' and
R'C(R")=C(R''')—(OCH$_2$CH$_2$)$_n$—R''''
where R', R", R''', and R'''' each independently represents H, a linear or branched alkyl having 1 to 5 carbons; and n is 2 to 5.

3. The device of claim 1, wherein said duty cycle is from about 1/10 to about 1/1000, and the pulse-on time is from about 1 msec to less than 100 µsec, and the pulse-off time is from about 10 µsec to less than 2000 msec.

4. The device of claim 1, wherein said organic compound is di(ethylene glycol) vinyl ether, di(ethylene glycol) divinyl ether, or di(ethylene glycol) methyl vinyl ether.

5. The device of claim 1, wherein said substrate is a contact lens.

6. The device of claim 1, wherein said gas phase polymerization is high voltage discharge, radio frequency, microwave; ionizing radiation induced plasma polymerization; or photo induced polymerization; or a combination thereof.

7. The device of claim 1, wherein said coating composition is gradient layered by systematically decreasing the duty cycle of said gas phase polymerization.

8. A device comprising a substrate and a coating composition, said coating composition being formed by the gas phase polymerization of a gas comprising at least one organic compound, said gas phase polymerization being pulsed, having a variable duty cycle each being of less than 1/5, in which the pulse-on time is less than 100 msec and the pulse-off time is less than 2000 msec, and said organic compound having the following structure:

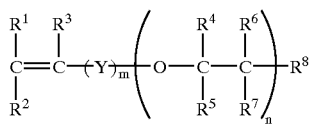

m = 0-1; n = 2-5, where Y represents C=O;
R$^1$, R$^2$, R$^3$, R$^4$, R$^5$, R$^6$ and R$^7$ each independently represents:
H,
OH,
halogen,
C$_1$-C$_4$ alkyl,
C$_1$-C$_4$ alkene,
C$_1$-C$_4$ diene,
C$_1$-C$_4$ alkyne,
C$_1$-C$_4$ alkoxy, or
C$_1$-C$_4$ alkyl halide; and
R$^8$ represents:
H,
halogen,
C$_1$-C$_4$ alkyl,
C$_1$-C$_4$ akene,
C$_1$-C$_4$ diene,
C$_1$-C$_4$ alkyne,
C$_1$-C$_4$ alkyl halide,
C$_1$-C$_4$ aldehyde,
C$_1$-C$_4$ ketone,
C$_1$-C$_4$ epoxide,
C$_1$-C$_4$ carboxylic acid,
C$_1$-C$_4$ ester,
—CH=CHR$^9$, where R$^9$ is H, halogen, C$_1$-C$_4$ alkyl, C$_1$-C$_4$ alkyl halide, C$_1$-C$_4$ aldehyde, C$_1$-C$_4$ ketone, C$_1$-C$_4$ alkoxyl, C$_1$-C$_4$ epoxide, C$_1$-C$_4$ carboxylic acid, or C$_1$-C$_4$ ester, or
—OR$^{10}$, where R$^{10}$ is H, halogen, C$_1$-C$_4$ alkyl, C$_1$-C$_4$ alkene, C$_1$-C$_4$ diene, C$_1$-C$_4$ alkyne, C$_1$-C$_4$ alkyl halide, C$_1$-C$_4$ aldehyde, C$_1$-C$_4$ ketone, C$_1$-C$_4$ epoxide, C$_1$-C$_4$ carboxylic acid, or C$_1$-C$_4$ ester.

9. The device of claim 8, wherein said organic compound is selected from the group consisting of:
R'C(R")=C(R''')—(OCH$^2$CH$^2$)$_n$—OR'''' and R'C(R")=C(R''')—(OCH$^2$CH$^2$)$_n$—R""

where R', R", R''', and R"" each independently represents H, a linear or branched alkyl having 1 to 5 carbons; and n is 2 to 5.

10. The device of claim 8, wherein said duty cycles vary from about 1/10 to about 1/1000, and the pulse-on time varies from about 1 μsec to less than 100 msec, and the pulse-off time varies from about 10 μsec to less than 2000 msec.

11. The device of claim 8, wherein said organic compound is di(ethylene glycol) vinyl ether, di(ethylene glycol) divinyl ether, or di(ethylene glycol) methyl vinyl ether.

12. The device of claim 8, wherein said substrate is a contact lens.

13. The device of claim 8, wherein said gas phase polymerization is high voltage discharge, radio frequency, microwave; ionizing radiation induced plasma polymerization; or photo induced polymerization; or a combination thereof.

14. The device of claim 8, wherein said coating composition is gradient layered by systematically decreasing the duty cycle of said gas phase polymerization.

* * * * *

UNITED STATES PATENT AND TRADEMARK OFFICE
CERTIFICATE OF CORRECTION

| | | |
|---|---|---|
| PATENT NO. | : 6,482,531 B1 | Page 1 of 1 |
| APPLICATION NO. | : 09/115860 | |
| DATED | : November 19, 2002 | |
| INVENTOR(S) | : Richard B. Timmons et al. | |

It is certified that error appears in the above-identified patent and that said Letters Patent is hereby corrected as shown below:

In the Specification

At Col. 1, line 13, delete

"The U.S. Government has certain rights in the present invention pursuant to the National Institutes of Health under Grant #R01AR43186-01 and by the Texas Higher Education Coordinating Board ATP Program under Grant #003656-137."

At Col. 1, line 13, add

--This invention was made with U.S. Government support under Grant #R01AR43186-01 awarded by the National Institutes of Health and under Grant #003656-137 awarded by the Texas Higher Education Coordinating Board ATP Program. The government has certain rights in this invention.--

Signed and Sealed this
Twelfth Day of August, 2014

Michelle K. Lee
*Deputy Director of the United States Patent and Trademark Office*